United States Patent
Thomson et al.

(10) Patent No.: US 10,555,883 B2
(45) Date of Patent: *Feb. 11, 2020

(54) ORAL CARE COMPOSITIONS AND METHODS OF USE

(71) Applicant: Colgate-Palmolive Company, New York, NY (US)

(72) Inventors: Paul Thomson, Piscatatway, NJ (US); Nihal Dogu, Dayton, NJ (US); Michael Prencipe, West Windsor, NJ (US); Amy Russo, Belle Mead, NJ (US); Hans Stettler, Basel (CH); Andre Michelle Morgan, Robbinsville, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/548,857

(22) PCT Filed: Jun. 24, 2016

(86) PCT No.: PCT/US2016/039226
§ 371 (c)(1),
(2) Date: Aug. 4, 2017

(87) PCT Pub. No.: WO2017/003856
PCT Pub. Date: Jan. 5, 2017

(65) Prior Publication Data
US 2018/0028423 A1    Feb. 1, 2018

Related U.S. Application Data

(60) Provisional application No. 62/187,801, filed on Jul. 1, 2015.

(51) Int. Cl.
| | |
|---|---|
| *A61K 8/44* | (2006.01) |
| *A61Q 11/00* | (2006.01) |
| *A61K 8/21* | (2006.01) |
| *A61K 8/27* | (2006.01) |
| *A61K 8/34* | (2006.01) |
| *A61K 8/362* | (2006.01) |
| *A61K 8/25* | (2006.01) |
| *A61K 8/365* | (2006.01) |

(52) U.S. Cl.
CPC .................. *A61K 8/44* (2013.01); *A61K 8/21* (2013.01); *A61K 8/25* (2013.01); *A61K 8/27* (2013.01); *A61K 8/345* (2013.01); *A61K 8/362* (2013.01); *A61K 8/365* (2013.01); *A61Q 11/00* (2013.01); *A61K 2800/28* (2013.01); *A61K 2800/92* (2013.01)

(58) Field of Classification Search
CPC ... A61K 8/44; A61K 8/21; A61K 8/27; A61K 8/25; A61K 8/362; A61Q 11/00
See application file for complete search history.

(56) References Cited

U.S. PATENT DOCUMENTS

| | | |
|---|---|---|
| 2,876,166 A | 3/1959 | Nebergall |
| 2,946,725 A | 7/1960 | Norris et al. |
| 3,095,356 A | 6/1963 | Moss |
| 3,852,414 A | 12/1974 | Adler et al. |
| 3,914,404 A | 10/1975 | Langer |
| 4,335,102 A | 6/1982 | Nakashima et al. |
| 4,469,674 A | 9/1984 | Shah et al. |
| 4,961,924 A | 10/1990 | Suhonen |
| 5,000,944 A | 3/1991 | Prencipe et al. |
| 5,017,363 A | 5/1991 | Suhonen |
| 5,094,842 A | 3/1992 | Riley |
| 5,096,702 A | 3/1992 | Rolla et al. |
| 5,188,820 A | 2/1993 | Cummins et al. |
| 5,258,173 A | 11/1993 | Waterfie D |
| 5,716,600 A | 2/1998 | Zahradnik et al. |
| 5,833,952 A | 11/1998 | Grigor et al. |
| 5,932,192 A | 8/1999 | Campbell et al. |
| 6,187,295 B1 | 2/2001 | Glandorf |
| 6,464,963 B1 | 10/2002 | Gambogi et al. |
| 6,652,841 B1 | 11/2003 | Brown et al. |
| 6,685,920 B2 | 2/2004 | Baig et al. |
| 6,696,045 B2 | 2/2004 | Yue et al. |
| 8,211,406 B2 | 7/2012 | Brig et al. |
| 8,906,347 B2 | 12/2014 | Strand et al. |
| 9,486,396 B2 | 11/2016 | Jaraez et al. |
| 2003/0165442 A1 | 9/2003 | Baig et al. |

(Continued)

FOREIGN PATENT DOCUMENTS

| | | |
|---|---|---|
| CA | 1136991 A1 | 12/1892 |
| CA | 2026907 A1 | 4/1991 |

(Continued)

OTHER PUBLICATIONS

Author Unknown, Colgate Enamel Health Whitening Toothpaste, Clean Mint Paste 5.5 oz (155g), drugstore.com, http://www.drugstore.com/colgate-enamel-health-whitening-toothpaste-clean-mint-paste/qxp532832?catid=183827, redirects to https://www.walgreens.com/store/c/colgate-enamel-health-whitening-toothpaste-clean-mint-paste/ID=prod6238066-product?dscmredirect=1, accessed Jul. 31, 2017.
Campbell, 2011, "Modern Stannous Fluoride Dentrifice: Q&A's for Dental Professionals," Hygiene Success, Catalyst Magazine, Issue 3, pp. 36-37.
Friberg, 1989, "Foam Stability in a Glycerol System," Journal of Colloid and Interface Science 127(2):573-582.

(Continued)

*Primary Examiner* — Lezah Roberts

(57) ABSTRACT

This invention relates to oral care compositions comprising a basic amino acid in free or salt from (e.g., free form arginine); zinc oxide and zinc citrate; and a fluoride source comprising stannous fluoride.

8 Claims, No Drawings

(56) References Cited

U.S. PATENT DOCUMENTS

| | | |
|---|---|---|
| 2004/0146466 A1 | 7/2004 | Baig et al. |
| 2007/0025928 A1 | 2/2007 | Glandorf et al. |
| 2008/0138298 A1 | 6/2008 | Glandorf et al. |
| 2012/0082630 A1 | 4/2012 | Haught et al. |
| 2012/0207686 A1 | 8/2012 | Fruge et al. |
| 2013/0078197 A1* | 3/2013 | Mello .............. A61K 8/19 424/54 |
| 2013/0209375 A1 | 8/2013 | Moya Argilagos et al. |
| 2013/0216485 A1 | 8/2013 | Campbell et al. |
| 2013/0280182 A1 | 10/2013 | Burgess et al. |
| 2013/0287709 A1 | 10/2013 | Maloney et al. |
| 2014/0086851 A1 | 3/2014 | Fisher et al. |
| 2014/0308324 A1 | 10/2014 | Midha et al. |
| 2015/0305993 A1 | 10/2015 | Rege et al. |
| 2015/0313813 A1 | 11/2015 | Rege et al. |
| 2015/0335554 A1 | 11/2015 | Pan et al. |
| 2016/0303010 A1 | 10/2016 | Prencipe et al. |
| 2016/0338921 A1 | 11/2016 | Prencipe et al. |
| 2017/0020795 A1 | 1/2017 | Maloney et al. |
| 2017/0348550 A1 | 12/2017 | Wilbens et al. |
| 2017/0367939 A1 | 12/2017 | Thomson et al. |
| 2017/0367948 A1 | 12/2017 | Thomson et al. |

FOREIGN PATENT DOCUMENTS

| | | |
|---|---|---|
| CA | 2634758 A1 | 7/2007 |
| CA | 2760445 A1 | 11/2010 |
| EP | 0658565 A1 | 6/1995 |
| WO | WO 1998/002135 | 1/1998 |
| WO | WO 2014/088572 | 6/2014 |
| WO | WO 2014/088575 | 6/2014 |
| WO | WO 2015/094849 | 6/2015 |
| WO | WO 2016/058140 | 4/2016 |

OTHER PUBLICATIONS

Huber Engineered Materials, "Guidelines for Choosing a Huber Cleaving Silica," http://www.hubermaterials.com/products/silica-and-silicates/dental-silicas/formulation-considerations/guidelines-for-choosing-a-huber-dental-cleaning-silica.aspx, accessed Mar. 25, 2015.

International Search Report and Written Opinion of the International Searching Authority in International Application No. PCT/US2016/039226, dated Aug. 26, 2016.

O'Neil, ed., et al., 2001, "Zinc Phosphate," The Merck Index 13th edition, p. 1812 Monograph No. 10205.

\* cited by examiner

ORAL CARE COMPOSITIONS AND METHODS OF USE

CROSS REFERENCE TO RELATED APPLICATIONS

This application claims the benefit of priority to U.S. provisional application 62/187,801, filed Jul. 1, 2015, the contents of which are incorporated herein by reference in their entirety.

FIELD

This invention relates to oral care compositions comprising arginine or salt thereof, zinc oxide and zinc citrate, and a fluoride source comprising stannous fluoride, as well as to methods of using and of making these compositions.

BACKGROUND

Oral care compositions present particular challenges in preventing microbial contamination. Arginine and other basic amino acids have been proposed for use in oral care and are believed to have significant benefits in combating cavity formation and tooth sensitivity.

Commercially available arginine-based toothpaste for example, contains arginine bicarbonate and precipitated calcium carbonate, but not fluoride. The carbonate ion is believed to have cariostatic properties, and the calcium is believed to form in complex with arginine to provide a protective effect.

However, the formulation of certain oral care compositions presents special challenges. For example, oral care compositions comprising arginine or basic amino acids may have a basic pH, increasing potential for microbial contamination compared to acidic formulations. Moreover, not all preservatives are active at higher pH. Some preservatives negatively affect the taste or aesthetics of the product. While certain preservatives, such as ethanol or parabens, are known to be effective at a range of pHs, these preservatives are not suitable for all products or all markets.

Accordingly, there is a need for improved preservative agents for use in oral compositions comprising basic amino acids.

BRIEF SUMMARY

It has been surprisingly found that the inclusion of amino acid, e.g., arginine in an oral care composition comprising a zinc oxide and/or zinc citrate, selected at certain concentrations and amounts, and a fluoride source, e.g. stannous fluoride, unexpectedly increases the antibacterial effect of oral care compositions in the oral cavity of a user. The current formulations offer the advantage of robust microbial protection without significantly interfering with the stability of the oral care composition and allow for the integration of a basic amino acid without compromising stannous and zinc availability and deposition in situ. The increased amount of available zinc and stannous aids in reducing bacterial colonization and biofilm development. Without being bound by any theory, it is believed that the presence of the amino acid may help to increase the amount of soluble zinc and stannous which can then has an increased effect on inhibiting bacterial growth in the oral cavity of a user.

In one aspect the invention is an oral care composition (Composition 1.0) comprising:

a. a basic amino acid in free or salt from (e.g., free form arginine);
  b. zinc oxide and zinc citrate;
  c. a fluoride source comprising stannous fluoride.

For example, the invention contemplates any of the following compositions (unless otherwise indicated, values are given as percentage of the overall weight of the composition)

1.1 Composition 1.0 wherein the basic amino acid has the L-configuration (e.g., L-arginine).
1.2 Any of the preceding compositions wherein the basic amino acid is arginine in free form.
1.3 Any of the preceding compositions wherein the basic amino acid is provided in the form of a di- or tri-peptide comprising arginine, or salts thereof
1.4 Any of the preceding compositions wherein the basic amino acid is arginine, and wherein the arginine is present in an amount corresponding to 0.1% to 15%, e.g., 0.1 wt % to 10 wt %, e.g., 0.1 to 5 wt %, e.g., 0.5 wt % to 3 wt % of the total composition weight, about e.g., 1%, 1.5%, 2%, 3%, 4%, 5%, or 8%, wherein the weight of the basic amino acid is calculated as free form.
1.5 Any of the preceding compositions wherein the amino acid is arginine from 0.1 wt. %-6.0 wt. %. (e.g., about 1.5 wt %).
1.6 Any of the preceding compositions wherein the amino acid is arginine from about 1.5 wt. %.
1.7 Any of the preceding compositions wherein the amino acid is arginine from 4.5 wt. %-8.5 wt. % (e.g., 5.0%).
1.8 Any of the preceding compositions wherein the amino acid is arginine from about 5.0 wt. %.
1.9 Any of the preceding compositions wherein the amino acid is arginine from 3.5 wt. %-9 wt. %.
1.10 Any of the preceding compositions wherein the amino acid is arginine from about 8.0 wt. %.
1.11 Any of the preceding compositions wherein the amino acid is L-arginine.
1.12 Any of the preceding compositions wherein the basic amino acid further comprises lysine (e.g., 2% wt., 3% wt., 4% wt., 5% wt., 6% wt.), (e.g., 4% wt.).
1.13 Any of the preceding compositions wherein the amino acid comprises lysine from 1.0 wt. %-6.0 wt. %.
1.14 Any of the preceding compositions wherein the amino acid comprises lysine from about 1.5 wt. %.
1.15 Any of the preceding compositions wherein the amino acid comprises lysine from about 4.0 wt. %.
1.16 Any of the preceding compositions wherein the amino acid comprises L-lysine.
1.17 Any of the preceding compositions wherein the amino acid comprises free form lysine.
1.18 Any of the preceding compositions wherein the amino acid is arginine or lysine in partially or wholly in salt form.
1.19 Composition 1.18 wherein the amino acid is arginine phosphate.
1.20 Composition 1.18 wherein the amino acid is arginine hydrochloride.
1.21 Composition 1.18 wherein the amino acid is arginine bicarbonate.
1.22 Composition 1.18 wherein the amino acid comprises lysine phosphate.
1.23 Composition 1.18 wherein the amino acid comprises lysine hydrochloride.
1.24 Composition 1.18 wherein the amino acid comprises lysine bicarbonate.

1.25 Any of the preceding compositions wherein the amino acid is arginine or lysine ionized by neutralization with an acid or a salt of an acid.

1.26 Any of preceding compositions wherein the composition is ethanol-free.

1.27 Any of the preceding compositions further comprising a fluoride source selected from: sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.28 Any of the preceding compositions wherein the fluoride source further comprises a fluorophosphate.

1.29 Any of the preceding compositions wherein the fluoride source further comprises sodium monofluorophosphate.

1.30 Any of the preceding compositions wherein the fluoride source further comprises sodium fluoride.

1.31 Any of the preceding compositions wherein the fluoride source is present in an amount of 0.1 wt. % to 2 wt. % (0.1 wt %-0.6 wt. %) of the total composition weight.

1.32 Any of the preceding compositions wherein the fluoride source provides fluoride ion in an amount of from 50 to 25,000 ppm (e.g., 750-7000 ppm, e.g., 1000-5500 ppm, e.g., about 500 ppm, 1000 ppm, 1100 ppm, 2800 ppm, 5000 ppm, or 25000 ppm).

1.33 Any of the preceding compositions wherein the fluoride source is stannous fluoride which provides fluoride in an amount from 750-7000 ppm (e.g., about 1000 ppm, 1100 ppm, 2800 ppm, 5000 ppm).

1.34 Any of the preceding compositions wherein the fluoride source is stannous fluoride which provides fluoride in an amount of about 5000 ppm.

1.35 Any of the preceding compositions wherein stannous fluoride is the only fluoride source.

1.36 Any of the preceding compositions wherein the fluoride source is sodium fluoride or sodium monofluorophosphate and which provides fluoride in an amount of about 1450 ppm.

1.37 Any of the preceding compositions wherein the pH is between 4.0 and 10.0, e.g., 5.0 to 8.0, e.g., 7.0 to 8.0.

1.38 Any of the preceding compositions further comprising calcium carbonate.

1.39 The composition of 1.38, wherein the calcium carbonate is a precipitated calcium carbonate high absorption (e.g., 20% to 30% by weight of the composition) (e.g., 25% precipitated calcium carbonate high absorption).

1.40 Any of the preceding compositions further comprising a precipitated calcium carbonate—light (e.g., about 10% precipitated calcium carbonate—light) (e.g., about 10% natural calcium carbonate).

1.41 Any of the preceding compositions further comprising an effective amount of one or more alkali phosphate salts, e.g., sodium, potassium or calcium salts, e.g., selected from alkali dibasic phosphate and alkali pyrophosphate salts, e.g., alkali phosphate salts selected from sodium phosphate dibasic, potassium phosphate dibasic, dicalcium phosphate dihydrate, calcium pyrophosphate, tetrasodium pyrophosphate, tetrapotassium pyrophosphate, sodium tripolyphosphate, disodium hydrogenorthophoshpate, monosodium phosphate, pentapotassium triphosphate and mixtures of any of two or more of these, e.g., in an amount of 0.01-20%, e.g., 0.1-8%, e.g., e.g., 0.1 to 5%, e.g., 0.3 to 2%, e.g., 0.3 to 1%, e.g about 0.01%, about 0.1%, about 0.5%, about 1%, about 2%, about 5%, about 6%, by weight of the composition.

1.42 Any of the preceding compositions comprising tetrapotassium pyrophosphate, disodium hydrogenorthophoshpate, monosodium phosphate, and pentapotassium triphosphate.

1.43 Any of the preceding compositions comprising a polyphosphate.

1.44 The composition of 1.42, wherein the polyphosphate is tetrasodium pyrophosphate.

1.45 The composition of 1.43, wherein the tetrasodium pyrophosphate is from 0.1-1.0 wt % (e.g., about 0.5 wt %).

1.46 Any of the preceding compositions further comprising an abrasive or particulate (e.g., silica).

1.47 Any of the preceding compositions wherein the silica is synthetic amorphous silica. (e.g., 1%-28% by wt.) (e.g., 8%-25% by wt.).

1.48 Any of the preceding composition wherein the silica abrasives are silica gels or precipitated amorphous silicas, e.g. silicas having an average particle size ranging from 2.5 microns to 12 microns.

1.49 Any of the preceding compositions further comprising a small particle silica having a median particle size (d50) of 1-5 microns (e.g., 3-4 microns) (e.g., about 5 wt. % Sorbosil AC43 from PQ Corporation Warrington, United Kingdom).

1.50 Any of the preceding compositions wherein 20-30 wt % of the total silica in the composition is small particle silica (e.g., having a median particle size (d50) of 3-4 microns) and wherein the small particle silica is about 5 wt. % of the oral care composition.

1.51 Any of the preceding compositions comprising silica wherein the silica is used as a thickening agent, e.g., particle silica.

1.52 Any of the preceding compositions further comprising a nonionic surfactant, wherein the nonionic surfactant is in an amount of from 0.5-5%, e.g, 1-2%, selected from poloxamers (e.g., poloxamer 407), polysorbates (e.g., polysorbate 20), polyoxyl hydrogenated castor oil (e.g., polyoxyl 40 hydrogenated castor oil), and mixtures thereof 1.53 Any of the preceding compositions, wherein the poloxamer nonionic surfactant has a polyoxypropylene molecular mass of from 3000 to 5000 g/mol and a polyoxyethylene content of from 60 to 80 mol %, e.g., the poloxamer nonionic surfactant comprises poloxamer 407.

1.54 Any of the preceding compositions further comprising sorbitol, wherein the sorbitol is in a total amount of 10-40% (e.g., about 23%).

1.55 Any of the preceding compositions, wherein the ratio of the amount of zinc oxide (e.g., wt. %) to zinc citrate (e.g., wt %) is from 1.5:1 to 4.5:1 (e.g., 2:1, 2.5:1, 3:1, 3.5:1, or 4:1).

1.56 Any of the preceding compositions, wherein the zinc citrate is in an amount of from 0.25 to 1.0 wt % (e.g., 0.5 wt. %) and zinc oxide may be present in an amount of from 0.75 to 1.25 wt % (e.g., 1.0 wt. %) based on the weight of the oral care composition.

1.57 Any of the preceding compositions wherein the zinc citrate is about 0.5 wt %.

1.58 Any of the preceding compositions wherein the zinc oxide is about 1.0 wt %.

1.59 Any of the preceding compositions where the zinc citrate is about 0.5 wt % and the zinc oxide is about 1.0 wt %.
1.60 Any of the preceding compositions further comprising an additional ingredient selected from: benzyl alcohol, Methylisothizolinone ("MIT"), Sodium bicarbonate, sodium methyl cocoyl taurate (tauranol), lauryl alcohol, and polyphosphate.
1.61 Any of the preceding compositions wherein the benzyl alcohol is present from 0.1-0.8 wt %., or 0.2 to 0.7 wt %, or from 0.3 to 0.6 wt %, or from 0.4 to 0.5 wt %, e.g. about 0.1 wt. %, about 0.2 wt. %, about 0.3 wt %, about 0.4 wt %, about 0.5 wt %, about 0.6 wt %, about 0.7 wt % or about 0.8 wt %.
1.62 The composition of 1.61 wherein the benzyl alcohol is about 0.4 wt %.
1.63 Any of the preceding compositions further comprising an additional stannous source selected from stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide, or a mixture thereof.
1.64 Any of the preceding compositions comprising polymer films.
1.65 Any of the preceding compositions comprising a flavoring, fragrance and/or coloring agent.
1.66 The composition of 1.65, wherein the flavoring agent is sodium saccharin, sucralose, or a mixture thereof
1.67 Any of the preceding compositions, wherein the composition comprises a copolymer.
1.68 The composition of 1.67, wherein the copolymer is a PVM/MA copolymer.
1.69 The composition of 1.68, wherein the PVM/MA copolymer comprises a 1:4 to 4:1 copolymer of maleic anhydride or acid with a further polymerizable ethylenically unsaturated monomer; for example, 1:4 to 4:1, e.g. about 1:1.
1.70 The composition of 1.68, wherein the further polymerizable ethylenically unsaturated monomer comprises methyl vinyl ether (methoxyethylene).
1.71 The composition of any of 1.67-1.70, wherein the PVM/MA copolymer comprises a copolymer of methyl vinyl ether/maleic anhydride, wherein the anhydride is hydrolyzed following copolymerization to provide the corresponding acid.
1.72 The composition of any of 1.67-1.71, wherein the PVM/MA copolymer comprises a GANTREZ® polymer (e.g., GANTREZ® S-97 polymer).
1.73 Any of the preceding compositions, wherein the composition comprises a thickening agents selected from the group consisting of carboxyvinyl polymers, carrageenan, xanthan, hydroxyethyl cellulose and water soluble salts of cellulose ethers (e.g., sodium carboxymethyl cellulose and sodium carboxymethyl hydroxyethyl cellulose).
1.74 Any of the preceding compositions further comprising sodium carboxymethyl cellulose (e.g., from 0.5 wt. % 1.5 wt. %).
1.75 Any of the preceding compositions comprising from 5% 40%, e.g., 10%-35%, e.g., about 15%, 25%, 30%, and 35% water.
1.76 Any of the preceding compositions comprising an additional antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, Zinc Chloride, Zinc Lactate, Zinc Sulfate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.
1.77 Any of the preceding compositions comprising an antioxidant, e.g., selected from the group consisting of Co-enzyme Q10, PQQ, Vitamin C, Vitamin E, Vitamin A, BHT, anethole-dithiothione, and mixtures thereof.
1.78 Any of the preceding compositions comprising a whitening agent.
1.79 Any of the preceding compositions comprising a whitening agent selected from a whitening active selected from the group consisting of peroxides, metal chlorites, perborates, percarbonates, peroxyacids, hypochlorites, and combinations thereof.
1.80 Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example, calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.
1.81 Any of the preceding compositions further comprising an agent that interferes with or prevents bacterial attachment, e.g. ethyl lauroyl arginiate (ELA) or chitosan.
1.82 Any of the preceding compositions comprising:
  a. about 1.0% zinc oxide
  b. about 0.5% zinc citrate
  c. about 1.5% L-arginine
  d. about 750-7000 ppm (e.g., about 1000 ppm, 1100 ppm, 2800 ppm, 5000 ppm) stannous fluoride; and
  e. about 5% small particle silica.
1.83 Any of the preceding compositions comprising:
  a. about 1.0% zinc oxide
  b. about 0.5% zinc citrate
  c. about 750-7000 ppm (e.g., about 1000 ppm, 1100 ppm, 2800 ppm, 5000 ppm) stannous fluoride; and
  d. about 39.2% glycerin.
1.84 Any of the preceding oral compositions, wherein the oral composition may be any of the following oral compositions selected from the group consisting of: a toothpaste or a dentifrice, a mouthwash or a mouth rinse, a topical oral gel, and a denture cleanser.
1.85 A composition obtained or obtainable by combining the ingredients as set forth in any of the preceding compositions.

A composition obtained or obtainable by combining the ingredients as set forth in any of the preceding compositions.

A composition for use as set forth in any of the preceding compositions.

The invention further comprises the use of sodium bicarbonate, sodium methyl cocoyl taurate (tauranol), MIT, and benzyl alcohol and combinations thereof in the manufacture of a Composition of the Invention, e.g., for use in any of the indications set forth in the above method of Composition 1.0, et seq.

DETAILED DESCRIPTION

As used herein, the term "oral composition" means the total composition that is delivered to the oral surfaces. The composition is further defined as a product which, during the normal course of usage, is not, the purposes of systemic administration of particular therapeutic agents, intentionally swallowed but is rather retained in the oral cavity for a time sufficient to contact substantially all of the dental surfaces and/or oral tissues for the purposes of oral activity. Examples of such compositions include, but are not limited to, toothpaste or a dentifrice, a mouthwash or a mouth rinse, a topical oral gel, a denture cleanser, and the like.

As used herein, the term "dentifrice" means paste, gel, or liquid formulations unless otherwise specified. The dentifrice composition can be in any desired form such as deep striped, surface striped, multi-layered, having the gel surrounding the paste, or any combination thereof. Alternatively, the oral composition may be dual phase dispensed from a separated compartment dispenser.

Basic Amino Acids

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

Accordingly, basic amino acids include, but are not limited to, arginine, lysine, serine, citrullene, ornithine, creatine, histidine, diaminobutanoic acid, diaminoproprionic acid, salts thereof or combinations thereof. In a particular embodiment, the basic amino acids are selected from arginine, citrullene, and ornithine.

In certain embodiments, the basic amino acid is arginine, for example, L-arginine, or a salt thereof.

Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

In certain embodiments, the basic amino acid is present in an amount corresponding to 0.1% to 15%, e.g., 0.1 wt % to 10 wt %, e.g., 0.1 to 5 wt %, e.g., 0.5 wt % to 3 wt % of the total composition weight, about e.g., 1%, 1.5%, 2%, 3%, 4%, 5%, or 8%, wherein the weight of the basic amino acid is calculated as free form.

Fluoride Ion Source

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., each of which are incorporated herein by reference. Representative fluoride ion sources used with the present invention (e.g., Composition 1.0 et seq.) include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. Where the formulation comprises calcium salts, the fluoride salts are preferably salts wherein the fluoride is covalently bound to another atom, e.g., as in sodium monofluorophosphate, rather than merely ionically bound, e.g., as in sodium fluoride. In certain embodiments, the sole fluoride source is stannous fluoride.

Surfactants

The invention may in some embodiments contain anionic surfactants, e.g., the Compositions of Composition 1.0, et seq., for example, water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomo-glyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or, for example sodium laureth-2 sulfate $(CH_3(CH2)_{10}CH_2(OCH_2CH_2)_2OSO_3Na)$; higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., $C_{6-30}$ alkyl. In particular embodiments, the anionic surfactant (where present) is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%, and optimal concentrations depend on the particular formulation and the particular surfactant. In one embodiment, the anionic surfactant is present at from 0.03% to 5% by weight, e.g., 1.5%.

In another embodiment, cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No.

3,535,421, to Briner et al., herein incorporated by reference. Certain cationic surfactants can also act as germicides in the compositions.

Illustrative nonionic surfactants of Composition 1.0, et seq., that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the invention comprises a nonionic surfactant selected from polaxamers (e.g., polaxamer 407), polysorbates (e.g., polysorbate 20), polyoxyl hydrogenated castor oils (e.g., polyoxyl 40 hydrogenated castor oil), and mixtures thereof.

Illustrative amphoteric surfactants of Composition 1.0, et seq., that can be used in the compositions of the invention include betaines (such as cocamidopropylbetaine), derivatives of aliphatic secondary and tertiary amines in which the aliphatic radical can be a straight or branched chain and wherein one of the aliphatic substituents contains about 8-18 carbon atoms and one contains an anionic water-solubilizing group (such as carboxylate, sulfonate, sulfate, phosphate or phosphonate), and mixtures of such materials.

The surfactant or mixtures of compatible surfactants can be present in the compositions of the present invention in 0.1% to 5%, in another embodiment 0.3% to 3% and in another embodiment 0.5% to 2% by weight of the total composition.

Flavoring Agents

The oral care compositions of the invention may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint.

The flavoring agent is incorporated in the oral composition at a concentration of 0.01 to 1% by weight.

Chelating and Anti-Calculus Agents

The oral care compositions of the invention also may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide least 0.1 wt. % pyrophosphate ions, e.g., 0.1 to 3 wt 5, e.g., 0.1 to 2 wt %, e.g., 0.1 to 1 wt %, e.g., 0.2 to 0.5 wt %. The pyrophosphates also contribute to preservation of the compositions by lowering water activity.

Polymers

The oral care compositions of the invention also optionally include one or more polymers, such as polyethylene glycols, polyvinyl methyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 1 19 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alphabeta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, xanthan gum, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Silica may also be available as a thickening agent, e.g., synthetic amorphous silica. Colloidal magnesium aluminum silicate or finely divided silica can be used as component of the thickening composition to further improve the composition's texture. In certain embodiments, thickening agents in an amount of about 0.5% to about 5.0% by weight of the total composition are used. Thickeners may be present in an amount of from 1 wt % to 15 wt %, from 3 wt % to 10 wt %, 4 wt % to 9 wt %, from 5 wt % to 8 wt %, for example 5 wt %, 6 wt %, 7 wt %, or 8 wt %.

Abrasives

Natural calcium carbonate is found in rocks such as chalk, limestone, marble and travertine. It is also the principle component of egg shells and the shells of mollusks. The natural calcium carbonate abrasive of the invention is typically a finely ground limestone which may optionally be refined or partially refined to remove impurities. For use in the present invention, the material has an average particle size of less than 10 microns, e.g., 3-7 microns, e.g. about 5.5 microns. For example, a small particle silica may have an average particle size (D50) of 2.5-4.5 microns. Because natural calcium carbonate may contain a high proportion of relatively large particles of not carefully controlled, which may unacceptably increase the abrasivity, preferably no more than 0.01%, preferably no more than 0.004% by weight of particles would not pass through a 325 mesh. The material has strong crystal structure, and is thus much harder and more abrasive than precipitated calcium carbonate. The tap density for the natural calcium carbonate is for example between 1 and 1.5 g/cc, e.g., about 1.2 for example about 1.19 g/cc. There are different polymorphs of natural calcium carbonate, e.g., calcite, aragonite and vaterite, calcite being preferred for purposes of this invention. An example of a commercially available product suitable for use in the present invention includes Vicron® 25-11 FG from GMZ.

Precipitated calcium carbonate is generally made by calcining limestone, to make calcium oxide (lime), which can then be converted back to calcium carbonate by reaction with carbon dioxide in water. Precipitated calcium carbonate has a different crystal structure from natural calcium carbonate. It is generally more friable and more porous, thus having lower abrasivity and higher water absorption. For use in the present invention, the particles are small, e.g., having an average particle size of 1-5 microns, and e.g., no more than 0.1%, preferably no more than 0.05% by weight of particles which would not pass through a 325 mesh. The particles may for example have a D50 of 3-6 microns, for example 3.8=4.9, e.g., about 4.3; a D50 of 1-4 microns, e.g. 2.2-2.6 microns, e.g., about 2.4 microns, and a D10 of 1-2 microns, e.g., 1.2-1.4, e.g. about 1.3 microns. The particles have relatively high water absorption, e.g., at least 25 g/100 g, e.g. 30-70 g/100 g. Examples of commercially available products suitable for use in the present invention include, for example, Carbolag® 15 Plus from Lagos Industria Quimica.

In certain embodiments the invention may comprise additional calcium-containing abrasives, for example calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate, and/or silica abrasives, aluminum silicate, calcined alumina, bentonite or other siliceous materials, or combinations thereof.

In certain embodiments, any silica suitable for oral care compositions may be used, such as precipitated silicas or silica gels. For example, the silica can also be small particle silica (e.g., Sorbosil AC43 from PQ, Warrington, United Kingdom). The composition preferable contains from 5 to 20 wt % small particle silica, or for example 10-15 wt %, or for example 5 wt %, 10 wt %, 15 wt % or 20 wt % small particle silica.

In another embodiment, the abrasive may be high cleaning precipitated silica having a pellicle cleaning ratio (PCR) of greater than 85 when tested at 20% loading is known in the art as high cleaning silica. Typically, high cleaning silica also has a mean particle size $d_{50}$ of from 5 to 15 μm and an oil absorption of from 40 to 120 $cm^3/100$ g silica. The cleaning efficacy of the precipitated silica is expressed using the pellicle cleaning ratio (PCR). This is typically measured at 20% silica loading. The high cleaning silica preferably has a PCR value of greater than 85. The efficacy of the precipitated silica can also be expressed with reference to its abrasive characteristic using the radioactive dentin abrasion (RDA). Ideally, RDA values for an oral composition should be below about 250 to protect tooth enamel/dentin. Methods of performing PCR and RDA are described in e.g., U.S. Pat. Nos. 5,939,051 and 6,290,933 and "In Vitro Removal of Stain With Dentifrice", G. K. Stookey et al., J. Dental Research, Vol. 61, pages 1236-9, November 1982." Typically, the precipitated silica has a mean particle size $d_{50}$ of from 5 to 15 μm and an oil absorption of from 40 to 120 $cm^3/100$ g silica. Examples of precipitated silica having a mean particle size $d_{50}$ of from 5 to 15 μm and an oil absorption of from 40 to 120 $cm^3/100$ g silica including commercially available silicas such as Zeodent® 103 and Zeodent® 105 (Huber Silica Americas).

The composition preferable contains from 5 to 20 wt % high cleaning precipitated silica, or for example 10-15 wt %, or for example 5 wt %, 10 wt %, 15 wt % or 20 wt % high cleaning precipitated silica.

The composition may also comprise an abrasive silica having an acid pH in the composition. For example, prophy silica available from Grace, offered as Sylodent™, can be used. The acidic silica abrasive is included in the dentifrice components at a concentration of about 2 to about 35% by weight; about 3 to about 20% by weight, about 3 to about 15% by weight, about 10 to about 15% by weight. For example, the acidic silica abrasive may be present in an amount selected from 2 wt. %, 3 wt. %, 4% wt. %, 5 wt. %, 6 wt. %, 7 wt. %, 8 wt. %, 9 wt. %, 10 wt. %, 11 wt. %, 12 wt. %, 13 wt. %, 14 wt. %, 15 wt. %, 16 wt. %, 17 wt. %, 18 wt. %, 19 wt. %, 20 wt. %.

A commercially available acidic silica abrasive is Sylodent 783 available from W. R. Grace & Company, Baltimore, Md. Sylodent 783 has a pH of 3.4-4.2 when measured as a 5% by weight slurry in water. For use in the present invention, the silica material has an average particle size of less than 10 microns, e.g., 3-7 microns, e.g. about 5.5 microns.

Water

Water is present in the oral compositions of the invention. Water, employed in the preparation of commercial oral compositions should be deionized and free of organic impurities. Water commonly makes up the balance of the compositions and includes 5% to 45%, e.g., 10% to 20%, e.g., 25-35%, by weight of the oral compositions. This amount of water includes the free water which is added plus that amount which is introduced with other materials such as with sorbitol or silica or any components of the invention. The Karl Fischer method is a one measure of calculating free water.

Humectants

Within certain embodiments of the oral compositions, it is also desirable to incorporate a humectant to reduce evaporation and also contribute towards preservation by lowering water activity. Certain humectants can also impart desirable sweetness or flavor to the compositions. The humectant, on a pure humectant basis, generally includes 15% to 70% in one embodiment or 30% to 65% in another embodiment by weight of the composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the compositions herein.

pH Adjusting Agents

In some embodiments, the compositions of the present disclosure contain a buffering agent. Examples of buffering agents include anhydrous carbonates such as sodium carbonate, sesquicarbonates, bicarbonates such as sodium bicarbonate, silicates, bisulfates, phosphates (e.g., monopotassium phosphate, dipotassium phosphate, tribasic sodium phosphate, sodium tripolyphosphate, phosphoric acid), citrates (e.g. citric acid, trisodium citrate dehydrate), pyrophosphates (sodium and potassium salts) and combinations thereof. The amount of buffering agent is sufficient to provide a pH of about 5 to about 9, preferable about 6 to about 8, and more preferable about 7, when the composition is dissolved in water, a mouthrinse base, or a toothpaste base. Typical amounts of buffering agent are about 5% to about 35%, in one embodiment about 10% to about 30%, in another embodiment about 15% to about 25%, by weight of the total composition.

The present invention in its method aspect involves applying to the oral cavity a safe and effective amount of the compositions described herein.

The compositions and methods according to the invention (e.g., Composition 1.0 et seq) can be incorporated into oral compositions for the care of the mouth and teeth such as toothpastes, transparent pastes, gels, mouth rinses, sprays and chewing gum.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Example 1—Representative Formulation

The following formulation illustrates one embodiment of the present disclosure. All values are weight percentages based on the total weight of the composition.

TABLE 1

Representative Formulation

| Component | Wt. % |
|---|---|
| Humectants | 20.0-60.0 |
| Abrasives (e.g., including abrasive and high cleaning silicas) | 10-40 |
| Anionic Surfactant | 1.0-3.0 |
| Amphoteric Surfactant | 0.5-1.5 |
| Flavoring/Fragrance/Coloring Agent | 0.5-5.0 |
| Polymers | 1.0-10.0 |
| pH Adjusting Agents | 1.0-10.0 |
| Zinc Citrate | 0.25-1.0 |
| Zinc Oxide | 0.75-1.25 |
| Stannous Fluoride | 0.1-1.0 |
| L-Arginine | 0.1-10 |
| Water | q.s. |
| Total Components | 100.0 |

Example 2—Chemical Stability

The chemical stability of compositions containing arginine was compared with the chemical stability of chemical compositions that do not contain arginine. Both Formulation 1 and Comparative Formulation 2 contained stannous fluoride, zinc citrate, and zinc oxide. Formulation 1 additionally comprised 1.5 arginine. Formulation 2 did not contain arginine. The results are summarized in Table 1 below.

Stability measurements in the form of presence of soluble zinc and soluble stannous were taken at the beginning of the testing period, after 4 weeks, after 8 weeks, and after 13 weeks. Initially, Formulation 1 contained a total stannous content of 0.31 wt. % and a total zinc content of 1.06 wt. %. Comparative Formulation 2 contained a total stannous content of 0.35 wt. % and a total zinc content of 1.06 wt. %. The soluble stannous and zinc values in the table represent the total stannous and zinc content that were present as ions in solution. The stability was measured under accelerated aging conditions at 40° C. At the end of the testing period (i.e., at 13 weeks), soluble stannousand zinc content was also measured at 25° C.

TABLE 2

Stability Data

| | Test | Initial | 4 weeks (40° C.) | 8 weeks (40° C.) | 13 weeks (25° C./ 40° C.) |
|---|---|---|---|---|---|
| Formulation 1 (containing arginine) | Ionic Fluoride | 1036 ppm | 921 ppm | 857 ppm | 995/742 ppm |
| | Soluble Stannous (wt. %) | 0.3% | 0.25% | 0.20% | 0.25/0.24% |
| | Soluble Zinc (wt. %) | 0.71% | 0.62% | 0.64% | 0.68/0.76% |
| | pH (10% solution) | 7.36 | 7.46 | 7.46 | 7.53 |

TABLE 2-continued

Stability Data

|  | Test | Initial | 4 weeks (40° C.) | 8 weeks (40° C.) | 13 weeks (25° C./ 40° C.) |
|---|---|---|---|---|---|
| Comparative Formulation 2 (no arginine) | Ionic Fluoride | 1087 ppm | 924 ppm | 762 ppm | 983/725 ppm |
|  | Soluble Stannous (wt. %) | 0.27% | 0.28% | 0.23% | 0.22/0.23% |
|  | Soluble Zinc (wt. %) | 0.65% | 0.66% | 0.59% | 0.58/0.60% |
|  | pH (10% solution) | 7.38 | 7.7 | 7.5 | 7.0 |

As clearly shown above, the soluble stannous and zinc in Formulation 1 showed very little degradation, even after 13 weeks under accelerated aging conditions (i.e., 40° C.).

Example 3—Stannous and Zinc Ion Delivery Studies

Stannous and zinc ion delivery was tested using an in vitro bovine enamel uptake assay and an in vitro Vitroskin metal ion uptake assay. The bovine enamel assay was designed to test for stannous and zinc delivery onto tooth surfaces, while the Vitroskin assay was designed to test for stannous and zinc delivery onto soft tissue surfaces in the oral cavity, such as gum surfaces. The results of these tests are summarized in Tables 3 and 4 below.

TABLE 3

Metal Ion Uptake on Bovine Enamel Surface

|  | Stannous Ion Uptake (ppm) | Zinc Ion Uptake (ppm) |
|---|---|---|
| Formulation 1 (containing arginine) | 0.57 | 3.27 |
| Comparative Formulation 2 (no arginine) | 0.59 | 3.08 |

The bovine enamel pieces tested are of uniform volumetric size. Therefore, results are reported in ppm uptake per bovine enamel piece. The results shown above indicate that stannous uptake in Formulation 1 which contained 1.5% arginine was not compromised and showed very little degradation by the presence of arginine, and was consistent with the formulation containing no arginine. Zinc uptake, on the other hand, was surprisingly shown to be statistically better in Formulation 1 than Comparative Formulation 2, which did not contain arginine.

TABLE 4

Metal Ion Uptake on Vitroskin Surface

|  | Stannous Ion Uptake (µg/cm2) | Zinc Ion Uptake (µg/cm2) |
|---|---|---|
| Formulation 1 (containing arginine) | 2.66 | 16.01 |
| Comparative Formulation 2 (no arginine) | 2.83 | 17.10 |

As shown above, the results demonstrate that Formulation 1 showed similarly favorable stannous and zinc uptake to Comparative Formulation 2. Vitroskin is a soft tissue mimetic, and has similar properties to human soft tissue. Therefore, it is expected that the stannous and zinc in the tested formulation will have efficient delivery to soft tissue in the oral cavity, such as gums, cheeks and tongue.

Example 4—Representative Dentifrice

In one representative formulation, a dentifrice comprises the following:
 a. 0.75 wt % to 1.25 wt % (e.g. 1.0 wt. %) zinc oxide
 b. 0.25 wt % to 1.0 wt % (e.g. 0.5 wt. %) zinc citrate
 c. 750-7000 ppm (e.g. 4500 ppm) stannous fluoride; and
 d. 0.1 wt % to 10 wt % (e.g. 1.5% wt. %) L-Arginine.

Based on the data shown above, this dentifrice unexpectedly provides improved metal ion uptake (e.g., Sn and Zn uptake) and reduce the amounts of bacterial cells in the oral cavity. Without being bound by any theory, it is believed that the presence of the amino acid allows for improved stannous and zinc deposition on surfaces without significant compromise to stannous uptake in the composition.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

While the present invention has been described with reference to embodiments, it will be understood by those skilled in the art that various modifications and variations may be made therein without departing from the scope of the present invention as defined by the appended claims.

What is claimed is:

1. An oral care composition comprising:
 a. a basic amino acid in free or salt form, wherein the amino acid is L-arginine in an amount of about 1.5 wt. %;
 b. zinc oxide and zinc citrate, wherein the zinc citrate is in an amount of about 0.5 wt. % and zinc oxide may be present in an amount of about 1.0 wt. % based on the total weight of the composition;
 c. a fluoride source comprising stannous fluoride, wherein the stannous fluoride is present in an amount from 0.1 wt. % to 2 wt. % based on the total weight of the composition, and wherein the stannous fluoride provides about 750-7000 ppm fluoride; and
 d. about 5% small particle silica, based on the total weight of the composition.

2. The oral care composition of claim 1 wherein the amino acid is arginine in free form.

3. The oral care composition of claim 1 wherein the amino acid is arginine partially or wholly in salt form.

4. The oral care composition of claim 1, wherein the fluoride source further comprises at least one member selected from the group of: sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

5. The composition of claim 1, wherein stannous fluoride provides soluble fluoride in an amount of about 1000-5500 ppm.

6. The composition of claim 1, wherein stannous fluoride provides soluble fluoride in an amount of about 5000 ppm.

7. The oral care composition of claim 1 further comprising:
   d. about 39.2% glycerin based on the total weight of the composition.

8. The oral care composition of claim 1, wherein the oral composition may be any of the following oral compositions selected from the group consisting of: a toothpaste or a dentifrice, a mouthwash or a mouth rinse, a topical oral gel, and a denture cleanser.

* * * * *